United States Patent [19]

Rohrschneider

[11] Patent Number: 5,643,888
[45] Date of Patent: Jul. 1, 1997

[54] REGULATING RETROVIRAL REPLICATION, INFECTION, AND PATHOGENESIS

[75] Inventor: Larry R. Rohrschneider, Mercer Island, Wash.

[73] Assignee: Fred Hutchinson Cancer Research Center, Seattle, Wash.

[21] Appl. No.: 334,188

[22] Filed: Nov. 3, 1994

Related U.S. Application Data

[63] Continuation of Ser. No. 122,022, Sep. 14, 1993, abandoned, which is a continuation of Ser. No. 784,145, Oct. 30, 1991, Pat. No. 5,264,356, which is a continuation of Ser. No. 53,306, filed as PCT/US86/02586 Nov. 26, 1986, abandoned, which is a continuation-in-part of Ser. No. 812,937, Dec. 23, 1985, abandoned.

[51] Int. Cl.$^6$ .......................... A41K 31/70; G01N 33/48
[52] U.S. Cl. .................. 514/43; 514/62; 514/299; 514/315; 514/348; 514/412; 514/413; 514/425; 514/934
[58] Field of Search ...................... 514/43, 62, 299, 514/315, 348, 412, 413, 425, 934

[56] References Cited

U.S. PATENT DOCUMENTS

| | | | |
|---|---|---|---|
| 4,837,237 | 6/1989 | Rohrschneider et al. | 514/62 |
| 4,857,315 | 8/1989 | Dennis | 424/85 |
| 5,004,746 | 4/1991 | Liu et al. | 514/299 |
| 5,051,407 | 9/1991 | Böshagen et al. | 514/24 |
| 5,264,356 | 11/1993 | Rohrschneider | 435/236 |

FOREIGN PATENT DOCUMENTS

| | | |
|---|---|---|
| 0202661A2 | 11/1986 | European Pat. Off. . |
| 0295538A2 | 12/1988 | European Pat. Off. . |
| 2166050A | 4/1986 | United Kingdom . |

OTHER PUBLICATIONS

Fischl et al, "The Safety and Efficacy of Combination N-Butyl-Deoxynojirimycin (SC-48334) and Zidovudine in Patients with HIV-1 Infection and 200-500 CDY Cells/mm$^3$", Journal of Aquired Immune Deficiency Syndromes, vol. 7, No. 2, 1994, pp. 139-147.

International Search Report dated Mar. 25, 1987 for related International Application No. PCT/US86/02586, filed Nov. 26, 1986.

Pinter, A., et al., Studies with Inhibitors of oligosaccharide processing indicate a functional role for complex sugars in the transport and proteolysis of Friend mink cell focus-inducing murine leukemia virus envelope proteins, Virology 136:196-210, 1984.

Schwartz, P.M., and A.D. Elbein, The effect of glycoprotein-processing inhibitors on fucosylation of glycoproteins, Journal of Biological Chemistry 260(27):14452-14458, 25 Nov. 1985.

Mitsuya, H., et al., Suramin protection of T cells in vitro against infectivity and cytopathic effect of HTLV-III, Science 226:172-174, 12 Oct. 1984.

Bosch, J.V., et al., The mannosidase inhibitors 1-deoxymannojirimycin and swainsonine have no effect on the biosynthesis and infectivity of Rous sarcoma virus, Virology 143:342-346, 1985.

Bosch, J.V., and R.T. Schwarz, Processing of gPr92$^{env}$, the percursor to the glycoproteins of Rous sarcoma virus: use of inihibitors of oligosaccaharide trimming and glycoprotein transport, Virology 132:95-109, 1984.

Gibson, R., et al., The nonglycosylated glycoprotein of vesicular stomatitis virus in temperature-sensitive and undergoes intracellular aggregation at elevated temperatures, Journal of Biological Chemistry 254(9):3600-3607, 1979.

Datema, R., and R.T. Schwarz, Effect of energy depletion on the glycosylation of a viral glycoprotein, Journal of Biological Chemistry 256(21):11191-11198, 1981.

Datema, R., et al., Inhibition of formation of complex oligosaccharides by the glucosidase inhibitor bromoconduritol, Proc. Natl. Acad. Sci. USA 79:6787-6791, 1982.

Kang, M.S., and A.D. Elbein, Alterations in the structure of the oligosaccharide of vesicular stomatitis virus G protein by swainsonine, Journal of Virology 46(1):60-69, 1983.

Romero, P.A., et al., N-methyl-1-deoxynojirimycin, a novel inhibitor of glycoprotein processing, and its effect of fowl plague virus maturation, Virology 130:238-242, 1983.

Elbein, A.D., Inhibitors of glycoprotein synthesis, Methods in Enzymology 98:135-154, 1983.

Pan, Y.T., et al., Castanospermine inhibits the processing of the influenza viral hemagglutinin, Fed. Proc. 42(7):2084, Abstract No. 1909, 1983.

Pan, Y.T., et al., Castanospermine inhibits the processing of the oligosaccharide portion of the influenza virus hemagglutinin, Biochemistry, pp. 3975-3984, 1983.

Schlesinger, S., et al., The formation of vesicular stomatitis virus (San Juan strain) becomes temperature-sensitive when glucose residues are retained on the oligosaccharides of the glycoprotein, Journal of Biological Chemistry 259(12):7597-7601, 1984.

Niemann, H., et al., Effects of trimming inhibitors of N-linked glycans on the maturation of mouse hepatitis virus (MHV), Gesellnschaft for Biologische Chemie 365:1040, Abstract No. A59, 1984.

Elbein, A. D., et al., The pyrrolidine alkaloid, 2, 5-Dihydroxymethyl-3, 4-dihydroxypyrrolidine, inhibits glycoprotein processing, Journal of Biological Chemistry 259(20):12409-12413, 25 Oct. 1984.

(List continued on next page.)

Primary Examiner—Nathan M. Nutter
Attorney, Agent, or Firm—Christensen O'Connor Johnson & Kindness PLLC

[57] ABSTRACT

Glucosidase I inhibitors as therapeutic agents for combatting nondefective retroviral pathogens, including the aetiological agents of AIDS and feline leukemia. Administration of a processing glucosidase I inhibitor, preferably castanospermine, interrupts the replication of the retrovirus in infected cells, alleviates pathogenic effects associated with the presentation of vital env glycoproteins on infected cells, and may furthermore prevent infection of target cells by interrupting expression of endogenous receptors recognized by the virion.

12 Claims, No Drawings

OTHER PUBLICATIONS

Schlesinger, S., et al., The effects of inhibitors of glucosidase I on the formation of Sindbis Virus Research 2:139–149, 1985.

Repp, R., et al., The effects of processing inhibitors of N–linked oligosaccharides on the intracellular migration of glycoprotein E2 of mouse hepatitis virus and the maturation of coronavirus particles, Journal of Biological Chemistry 260(29):15873–15879, 15 Dec. 1985.

Seccombe, M., Rainforest tree seed may hold key to cancer cure, The Weekend Australia, Issue No 6807 of 12–13 Jul. 1986, at p. 3.

Walker, B. D., et al., Anti–HIV properties of castanospermine, III International Conference on AIDS, Washington D.C., Jun. 1–5, 1987.

Hibbard, R., Area scientist finds promising anti–AIDS drug, p. A6, Seattle Post–Intelligencer, Aug. Aug. 29, 1987.

Drug derived from chestnuts may stop AIDS, Journal American, Aug. 30, 1987.

Nucleus, p. 6, Fred Hutchinson Cancer Research Center, Oct. 1987.

NIAID may fund a total of 16 AIDS drug discovery groups, AIDS Update, pp. 3–4, Sep. 18, 1987.

Walker, B. D., et al., Inhibition of human immunodeficiency virus syncytium formation and virus replication by castanospermine, Proc. Natl. Acad. Sci. USA 84:8120–8124, Nov. 1987.

Tyms, A.S., et al., Castanospermine and other plant alkaloid inhibitors of glucosidase activity block the growth of HIV, The Lancet, pp. 1025–1026, Oct. 31, 1987.

Gruters, R. A., et al., Interference with HIV–induced syncytium formulation and viral infectivity by inhibitors of trimming glucosidase, Nature 330:74–77. 5 Nov. 1987.

Hixson, J.R., Chemoprophylaxis predicted to be effective against AIDS until vaccine is developed, Oncology Times 10(3):1,4, Feb. 1, 1988.

Hohenschutz, L. D., et al., Castanospermine, 1, 6, 7, 8–tetrahydroxyoctahydroindolizine alkaloid, from seeds of *Castanospermum australe*, Phytochemistry 20(4):811–814, 1981.

Hori, H., et al., Inhibition of processing of plant N–linked oligosaccharides by castanospermine, Archives of Biochemistry and Biophysics 228(2):525–533, 1984.

Chung, K.–N., et al., Swainsonine and castanospermine blockade of mannose glycoprotein uptake by macrophages, The Journal of Biological Chemistry 259(23):14637–14641, 1984.

Saul, R., et al., Castanospermine inhibits αglucosidase activities and alters glycogen distribution in animals, Proc. Natl. Acad. Sci. USA 82:93–97, Jan. 1985.

Sasak, V. W., et al., Castanospermine inhibits glucosidase I and glycoprotein secretion in human hepatoma cells, Biochem. J. 232:759–766, 1985.

Fuhrmann, U., et al., Review: Inhibtors of oligosaccharide processing, Biochimica et Biophysica Acta 825:95–110, 1985.

Palamarczyk, G., and A. D. Elbein, The effect of castanospermine on the oligosaccharide structures of glycoproteins from lymphoma cell lines, Biochem. J. 227:795–804, 1985.

Nichols, E. J., et al., Transformation by the v–fms oncogene product: role of glycosylational processing and cell surface expression, Molecular and Cellular Biology 5(12):3467–3475, 1985.

Trugnan, G., et al., Castanospermine: a potent inhibitor of sucrase from the human enterocyte–like cell line Caco–2, FEBS letters 195(1,2):28–32, Jan. 1986.

Hadwiger, A., et al., Appropriate glycosylation of the *fms* gene product is a prerequisite for its transforming potency, The EMBO Journal 5(4):689–694, 1986.

Scofield, A. M., et al., Inhibition of mammalian digestive disaccharidases by polyhydroxy alkaloids, Life Sciences 39:645–650, 1986.

Humphries, M. J. et al., Inhibition of experimental metastasis by castanospermine in mice; blockage of two distinct stages of tumor colonization by oligosaccharide processing inhibitors, Cancer Research 46:5215–5222, Oct. 1986.

Gross, V., et al., Different effects of the glucosidase inhibitors 1–deoxynojirimycin, N–methyl–1–deoxynojirimycin and castanospermine on the glycosylation of rat $\alpha_1$–proteinase inhibitor and $\alpha_1$–acid glycoprotein, Biochem. J. 236:853–860, 1986.

Spearman, M. A. et al., Studies on the effect of glycoprotein processing inhibitors on fusion of L6 myoblast cell lines, Experimental Cell Research 168:116–126, 1987.

Hubbard, S. C., and P. W. Robbins, Synthesis and processing of protein–linked oligosaccharides in vivo, Journal of Biological Chemistry 254(11):4568–4576, 1979.

Schwarz, R. T., and R. Datema, Inhibitors of protein glycosylation, TIBS, pp. 65–67, Mar. 1980.

Tulsiani, D.R.P., et al., Swainsonine inhibits the biosynthesis of complex glycoproteins by inhibition of golgi mannosidase II, Journal of Biological Chemistry 257(14):7936–7939, 1982.

Saunier, B., et al., Inhibition of N–linked complex oligosaccharide formation by 1–deoxynojirimycin, and inhibitor of processing glucosidases, Journal of Biological Chemistry, 257(23):14155–14161, 1982.

Gross, V., et al., Effect of swainsonine on the processing of the asparagine–linked carbohydrate chains of $\alpha_1$–antitrypsin in rat hepatocytes, Journal of Biological Chemistry, 258(6):4032–4036, 1983.

Peyrieras, N., et al., Effects of the glucosidase inhibitors nojirimycin and deoxynojirimycin on the biosynthesis of membrane and secretory glycoproteins, The EMBO Journal 2(6):823–832, 1983.

Tulsiani, D.R.P., and O. Touster, Swainsonine causes the production of hybrid glycoproteins by human skin fibroblasts and rat liver golgi preparations, Journal of Biological chemistry 258(12):7578–7585, 1983.

Arumugham, R. G. and M. L. Tanzer, Abnormal glycosylation of human cellular fibronectin in the presence of swainsonine, Journal of Biological Chemistry 258(19):11883–11889, 1983.

Fuhrmann, U., et al., Novel mannosidase inhibitor blocking conversion of high mannose to complex oligosaccharides, Nature 307:755–758, 23 Feb. 1984.

Lemansky, P., et al., Cathepsin D and βhexosaminidase snthesized in the presence of 1–deoxynojirimycin accumulate in the endoplasmic reticulum, Journal of Biological Chemistry 259(16):10129–10135, 1984.

Olden, K., et al., Function of glycoprotein glycans, TIBS 10:78–82, 1985.

Joubert, P. H., et al., Effect of an alpha–glucosidase inhibitor (BAY m 1099) on post–prandial blood glucose and insulin in Type II diabetics, Eur J Clin Pharmacol 30:253–255, 1986.

Schnack, Ch., et al., Effects of the αglucosidase inhibitor 1 desoxynojirimycin (BAY M 1099) on postprandial blood glucose, serum insulin and C–peptide levels in Type 11 diabetic patients, Eur J Clin Pharmacol 30:417–419, 1986.

Joklik et al. (eds) (1980) in: 17th Edition Zinsser Microbiology, Appleton–Century–Crofts, New York, NY, pp. 1018–1021, 1119–1121, 1125–1136.

Trainin et al. (1983) Science 220, 858–859.

Metcalf, D. (1985) Science 229, 16–22.

Datema, R., et al., On the role of oligosaccharide trimming in the maturation of sindbis of influenza virus, Archives of Virology 81:25–39, 1984.

Blough, H.A. et al., Glycosylation inhibitors block the expression of LAV/HTLV–111 (HIV) glycoproteins, Biochem. Biophys. Res. Comm. 141(1):33–38, Nov. 1986.

McDowell, W., et al., Glucose trimming and mannose trimming affect different phases of the maturation of sindbis virus in infected BHK cells, Virology 161:37–44, 1987.

Taylor, D.L., et al., Loss of cytomegalovirus infectivity after treatment with castanospermine or related plant alkaloids correlates with aberrant glycoprotein synthesis, Antiviral Research 10:11–26, 1988.

Montefiori, D.C., et al., Antibody–independent, complement–mediated enhancement of HIV–1 infection by mannosidase I and 11 inhibitors, Antiviral Research 11:137–146, 1989.

Tyms, A.S., and D.L. Taylor, Activity of glucosidase inhibitors against HIV infections, J. Antimicrobial Chemotherapy 22:271–274, 1988.

Montefiori, D.C., et al., Role of protein N–glycosylation in pathogensesis of human immunodefciency virus type 1, Proc. Natl. Acad. Sci. USA 85:9248–9252, Dec. 1988.

Pal, R., et al., Processing and secretion of envelope glycoproteins of human immunodefiency virus type 1 in the presence of trimming glucosidase inhibitor deoxynojirimycin, Intervirology 30:27–35, 1989.

Montefiori, D.C., et al., In vitro evaluation of mismatched double–stranded RNA (Ampligen) for combination therapy in the treatment of acquired immunodeficiency syndrome, AIDS research and Human Retroviruses 5(2):193–203, 1989.

Marx, J.L., AIDS drugs–coming but not here, Science 244:287, 21 Apr. 1989.

Poss, M.L., et al., Posttranslational modifications distinguish the envelope glycoprotein of the immunodeficiency disease–inducing feline leukemia virus retrovirus, J. Virology 63(1):189–195, Jan. 1989.

Webster's Ninth New Collegiate Dictionary, 1983, Merriam–Webster, Inc., MA., pp. 618–619.

Brock, T.D., 1979 in Biology of Microorganisms, Prentice–Hall, Inc. New Jersey, p. 346.

Salzman (ed.) 1986 in: Animal Models of Retrovirus Infection and Their Relationship to AIDS. Academic Press, Inc., Florida, pp. 3–13.

Haseltine et al., 1988. Scientific American 259, 52–58, 60, and 62.

Weber et al., 1988, Scientific American 101–104, 106, 108–109.

Yarchoan et al., 1988, Scientific American 259, 110–119.

Mitsuya, H., et al., Molecular targets for AIDS therapy, Science 249:1533–1544, 28 Sep. 1990.

Johnson, V.A., et al., Synergistic inhibition of human immunodeficiency virus type 1 and type 2 replication in vitro by castanospermine and 3'–azido–3'–deoxythymidine, Antimicrobial Agents and Chemotherapy 33(1):53–57, Jan. 1989.

Jones, .I.M., and G.S. Jacob, Anti–HIV drug mechanism, Nature 352:198, 18 Jul. 1991.

Ruprecht, R.M., Murine models for anti–viral therapy, Intervirology 30(suppl 1)2–11, 1989.

Ruprecht, R.M. et al., In vivo analysis of castanospermine, a candidate antiretroviral agent, Journal of Acquired Immune Deficiency Syndromes 2:149–157, 1989.

Ruprecht, R.M., et al., Castanospermine vs. its 6–O–butanoyl analog: a comparison of toxicity and antiviral activity in vitro and in vivo, Journal of Acquired Immune Deficiency Syndromes 4:48–55, 1991.

Chu, C.K., et al., J. Med. Chem. 32:612–617, 1989.

REGULATING RETROVIRAL REPLICATION, INFECTION, AND PATHOGENESIS

This is a continuation of application Ser. No. 08/122,022, filed Sep. 14, 1993, and now abandoned which is a continuation of application Ser. No. 07/784,145, filed Oct. 30, 1991 (U.S. Pat. No. 5,264,356), which is a continuation of application Ser. No. 07/053,306, filed May 22, 1987 and now abandoned and a continuation-in-part of application No. PCT/US86/02586, filed Nov. 26, 1986, which is a continuation-in-part of application Ser. No. 06/812,937, filed Dec. 23, 1985 and now abandoned the benefit of the filing dates of which are hereby claimed under 35 U.S.C. §120.

This invention was made with government support under grant CA-40987 awarded by the National Institutes of Health. The government has certain rights in the invention.

FIELD OF THE INVENTION

This invention relates to the therapeutic use of processing glucosidase inhibitors to regulate the replication, infection, and pathogenesis of animal retroviruses such as the aetiological agents of human acquired immune deficiency syndrome (AIDS), feline leukemia, equine infectious anemia, and chronic lentiviral diseases.

BACKGROUND OF THE INVENTION

Retroviruses are widespread in nature, sad infection with these agents is associated with neoplastic and other disease states in many vertebrates. Infection with nondefective retroviruses (i.e., encoding for at least the gag, pol, and env genes; but not for oncogenes) can induce neoplastic disease in a variety of animal species. For a review, see Pathogenesis of retrovirus-induced diseases, in Molecular Biology of Tumor Viruses: RNA tumor viruses, 2nd Ed., R. Weiss, N. Teich, H. Varmus and J. Coffin (eds), New York, Cold Spring Harbor Laboratory, 1984, pp. 785–998, hereby incorporated by reference. For example, lymphoid leukosis viruses (LLV), including the aetiological agent of avian leukosis, severely impact the poultry industry. Bovine leukemia virus (BLV), which is related to the human HTLV-I retrovirus discussed below, infects dairy herds, causing the disease known as enzootic bovine leukosis or lymphosarcoma in cattle. The retroviral agent (FeLV) of feline leukemia is also of significant veterinary concern. Other members of the retrovirus group, called lentiviruses, cause slowly progressive lethal diseases in sheep and goats, and possibly in humans.

Exogenous human retroviruses were recently discovered and have already been implicated as the aetiological agents of certain types of human leukemias and acquired immune deficiency syndrome (AIDS). HTLV-I (or ATLV) infects lymphocytes containing the OKT4 cell surface antigen and causes excessive proliferation of Impaired cells leading to a syndrome called adult T-cell leukemia (ATL). A second, related virus designated HTLV-II is associated with less aggressive T-cell leukemias. A third human retrovirus (HTLV-III, LAV, ARV, or HIV) also has tropism for OKT4$^+$ helper but instead of excessive proliferation HTLV-III induces a cytopathic effect leading to depletion of the target cell population and resultant immunosuppression. The development of AIDS and pro-AIDS syndrome requires continuous infection and replication of HTLV-III in OKT4$^+$ target cells. The genetic structures of these human retroviruses and the mechanisms by which they usurp host cell functions are considered novel among retroviruses; Wong-Staal and Gallo, Nature 317:395–403, 1985, hereby incorporated by reference.

One problem encountered during preclinical studies of the immunosuppressire viruses is that a dramatic loss of T-cell viability is noted within two to three weeks of infection with HTLV-III. As a result, special OKT4$^+$clones must be used that constitutively are at least partially resistant to the cell-killing effects of the retrovirus. A question then arises as to the applicability of negative controls (in terms of 100% cycopathic effect) in these systems. On the other hand, suitable positive controls (in terms of 100% inhibition of cytopathic effect) by which the efficacy of an experimental intervention can be monitored in vitro are also lacking.

Furthermore, no definitive therapy exists for the disease states associated with retroviral pathogens.

SUMMARY OF THE INVENTION

A processing glucosidase I inhibitor, preferably castanospermine, is administered to interrupt the replication of nondefective retroviruses in infected mammalian cells. As the replication of intact virions is necessary for continued in vivo transformation, and in many eases for pathogenic effect, the disclosed glucosidase I inhibitors are considered to be promising therapeutic agents for combatting nondefective retroviruses, including the aetiological agents of acquired immune deficiency syndrome (AIDS), feline leukemia (FeLV), equine infectious anemia (EIAV), and chronic lentiviral diseases such as visna in sheep and goats. The glucosidase I inhibitor may also serve to directly alleviate the pathogenic effects of retroviral infection where such effects require the presentation of normally glycosylated env proteins on the surface of infected cells. The glucosidase I inhibitor may also prevent retroviral infection of certain mammalian cells by interrupting the expression of endogenous receptor glycoproteins, normally recognized by the retroviral virion, on the surface of the target cells.

DETAILED DESCRIPTION OF THE PREFERRED EMBODIMENT

Pursuant to the invention, a glucosidase I inhibitor is administered to regulate retroviral (including lentiviral) replication in an animal host or cultured cells. The glucosidase I inhibitor may be selected from the group of castanospermine (1,6,7,8-tetrahydroxyoctahydroindolizine), N-methyl-1-deoxynojirimycin, 1-deoxynojirimycin, and 2,5-dihydroxymethyl-3,4-dihydroxypyrrolidine (which is here considered a glucosidase I inhibitor). In vivo administration can be via the bloodstream, peritoneal cavity, tousle, or alimentary canal. The glucosidase I inhibitor, preferably castanospermine or N-methyl-1-deoxynojirimycin, interrupts the normal processing of N-linked oligosaccharide chains on retroviral glycoproteins in infected cells. Normally, oligosaccharide structures are added en bloc to specific asparagine residues during the synthesis of the vital envelope (env) glycoproteins within the endoplasmic reticulum (ER) of an infected cell. For example, at least 10 such potential sites for addition of N-linked carbohydrate chains exist within the any protein of HTLV-III or FeLV (subgroup A). This initial oligosaccharide structure (Glc$_3$Man$_9$GlcNAc$_2$) is immediately processed within the endoplasmic reticulum by enzymatic removal of the three terminal glucose residues initiated by the ER enzyme glucosidase I. Normal processing would then continue after transfer to the Golgi compartment. However, inhibition of ER glucosidase I by specific inhibitors such as those listed above presumably blocks transfer to the Golgi and further processing. The net result is reduced expression of a functional env protein at the cell surface, and the production of infectious virus particles (virions) is inhibited. The defective env proteins could be either abnormally glycosylated or uncleaved precursor proteins, when made in the presence of the glucosidase I inhibitor. Spread of the virus within the target cell population is reduced or prevented, with reduction of pathogenic effect.

Administration of the glucosidase I inhibitor may also serve to directly alleviate the pathogenic effects of retroviral infection where such effects require the presentation of normally glycosylated any proteins on the surface of infected cells. For example, the abnormally glycosylated HTLV-III env proteins that result from castanospermine treatment may not be available for binding to the T4 receptors on other T cells, thus preventing the cell fusion or autofusion that has been implicated with the cytopathic effect of AIDS. See: Lethal actions of the AIDS virus debated, Sciences 233:282–283, 18 Jul. 1986.

The glucosidase I inhibitor may also or alternatively interrupt the normal expression, on uninfected target cells, of the endogenous cell surface glycoprotein antigen that acts as a receptor for the vital infection. Representative of such receptors are the OKT4 antigen and other T4 epitopes on human lymphocytes and other target cells of HTLV-III. Because these normal cellular antigens also contain carbohydrate, the glucosidase inhibitors can inhibit their expression by a mechanism similar to that described above for the viral env proteins. Reducing the cell surface expression of the glycoprotein receptor antigen in castanospermine-treated cells prevents or inhibits virus adsorption and infection. Even if the endogenous antigen is expressed on castanospermine-treated target cells, its carbohydrate may be altered enough to prevent or impair recognition by complementary structures on the virion.

In cell culture, the glucosidase I inhibitor can be added to culture medium at a dosage effective to regulate the effects of infection of the cultured cells by a pathogenic retrovirus. For example, positive controls (in terms of 100% inhibition of pathogenic effect) can be prepared for preclinical studies of HTLV-III and other T-lymphotrophic retroviruses by culturing cells expressing a T4 epitope with castanospermine at a dosage effective to substantially prevent replication of the retrovirus in infected cultured cells. Retroviral infection may be substantially prevented by castanospermine interrupting the cell surface expression of OKT4 antigen on the cultured cells. Retroviral replication may be substantially prevented by castanospermine interrupting the normal carbohydrate processing of HTLV-III vital glycoproteins. Negative controls (in terms of less than 100% pathogenic effect) are provided by adjusting the castanospermine to a level effective to render the cultured cells at least partially resistant to a pathogenic effect of retroviral infection. In this way preclinical studies of the AIDS-associated family of viruses need not be restricted to mutant T-lymphocyte clones but can embrace other, including patient-specific, cell lines. A culture medium for such clinical work includes an assimilable nutrient medium, typically also a growth factor such as interleukin-2 or T-cell growth factor, and a glucosidase I inhibitor at a dosage effective to regulate the effects of infection by the human retrovirus.

For in vivo treatment, the glucosidase I inhibitor, preferably castanospermine, is preferably administered in conjunction with a hematopoietic growth factor. Hematopoiesis, or the formation of blood cells, is a complex process involving controlled development of several blood cell lineages from a common bone marrow stem cell population. T cells, "B-cells", granulocytes, macrophages, platelets, eosinophils, and erythroeytes all originate from this common self-generating bone marrow pool, and their growth and development along each lineage is controlled by growth factors specific for one or a few of the lineages. These growth factors are soluble glycoproteins produced and secreted by both hematopoietic and nonhematopoietic cells (e.g., fibroblasts, endothelial cells), whose activities were originally detected by their ability to stimulate colonies of bone marrow cells to grow in soft agar assays. These factors have therefore been termed the colony stimulating factors (CSFs). Several such growth factors have been identified and purified, and, in general, named according to the cell lineages that they stimulate. GM-CSF stimulates granulocyte and macrophage development, G-CSF is specific for the granulocyte lineage, M-CSF (or CSF-1) is specific for the macrophage lineage, multi-CSF (also called interleukin-3) stimulates many cell lineages, and erythropoietin specifically stimulates the growth and development of erythrocytes; see The Hemopoietic Colony Stimulating Factors, by D. Metcalf, Elsevier, 1984, and D. Metcalf, The granulocyte-macrophage colony-stimulating factors, Science 229:16–22, 1985, both hereby incorporated by reference.

A potential side effect with the use of castanospermine for in vivo therapy is the possible depletion of hematopoietic cell populations. Castanospermine inhibits glycosylational processing of the carbohydrate components of glycoproteins and might interfere with the function of either specific CSFs or their receptors on target cells, as both the growth factors and receptors are glycoproteins. This inhibition may be an advantage if macrophage development is prevented, because a reservoir of HIV producing cells would be eliminated. On the other hand, a more general depletion of the blood cells by the actions of castanospermine would be deleterious and impair overall immune function. Such side effects have been a major problem in treating AIDS patients with AZT (3'-azido-3'-deoxythymidine).

It is therefore contemplated that the combined use of castanospermine with various colony stimulating factors will eliminate or alleviate the potential side effects of the glucosidase I inhibitor and provide a much more effective treatment. The colony stimulating factors build up the various hematopoietic cell populations while the castanospermine substantially prevents infection and spread of HIV. The CSFs and castanospermine can be administered intravenously, either simultaneously or in alternating or separate regimens.

The growth factor GM-CSF is currently considered to be the preferred CSF for combination therapy with castanospermine. GM-CSF stimulates the granulocyte, macrophage, and eosinophil cell lineage that are inhibited by castanospermines, and so would complement castanospermine in the disclosed treatment. Human GM-CSF has been cloned and sufficient amounts are potentially available for this type of therapy. A combination therapy of GM-CSF (or GM-CSF plus other CSFs) plus castanospermine would stimulate and maintain sufficient quantities of hematopoietie cell is to provide a competent immune system in a patient, while the castanospermine would substantially prevent further spread and cytopathic effects of HIV.

A combination of castanospermine and immunotherapy also would be of benefit for the treatment and possible elimination of HIV producing cells. Castanospermine prevents proper glycosylational processing of the HIV envelope glycoproteins but does not prevent virus replication. The virus produced in the presence of castanospermine is however not fully infectious due to defects in fusion with target CD4 positive cells. A combination of castanospermine treatment plus immunotherapy with antibodies to HIV envelope proteins (including, in some embodiments, castanospermine-modified envelope glycoproteins) would effectively prevent further infection and would foster the attack of existing cells that harbor HIV envelope proteins on their cell surfaces. The antibodies to HIV envelope proteins could be either monoclonal generated to HIV envelope determinants (passive therapy), or antibodies produced by AIDS patients by active immunization with purified viral proteins or molecular constructs (e.g., with a vaccinia virus expression system) that express proteins of the envelope glycoproteins.

Synergistic effects may also result from the actions of castanospermine in combination with other agents that block virus infection and/or replication at a point other than that at which castanospermine acts. Thus, effective combination therapies may include castanospermine in combination with other antiviral agents, especially antivirals that act at early stages of retroviral replication.

The following Examples are provided to illustrate the advantages and to assist one of ordinary skill in making and using the invention. The Examples are not intended in any way to otherwise limit the scope of the disclosure and the protection granted by Letters Patent hereon.

EXAMPLE 1

Effect of castanospermine (CA) on the synthesis of HTLV-III envelope proteins.

HTLV-III infected cells, e.g., H9 cells (or CEM cells), are cultured in the presence or absence of castanospermine (10–500 µg/ml CA; CALBIOCHEM, Behring Diagnostics, LaJolla, Calif.) for 2, 4, or 6 days, then assayed for expression of HTLV-III envelope proteins gp 120 and gp41.

The expression of the glycoproteins can be tested by Western blotting, by immune precipitation analysis, or by fluorescent antibody techniques using antibodies specific for the HTLV-III glycoproteins. For Western blotting analysis, the unlabeled cells are extracted with a detergent-containing buffer, and the proteins are separated on a polyacrylamide gel. After electrophoretic transfer to nitrocellulose paper, the individual viral glycoproteins are detected by autoradiography using the appropriate antibody and $^{125}$-I labeled; Protein A as described in J. Biol. Chem. 258:11219–11228, 1983 (hereby incorporated by reference). For immune precipitation; analysis, cells are labeled (2 hr) with $^{35}$S-methionine (50 mCi/ml) and extracted with detergent-containing buffer. The radiolabeled viral glycoproteins are identified in the extract by standard immune precipitation techniques using antibodies specific for these proteins. The proteins are separated by polyacrylamide gel electrophoresis and visualized by autoradiography of the dried gel as detailed in the above publication.

To detect the viral glycoproteins on the surface of the infected cells such as H9 cells, antibodies specific for envelope protein (mainly gp120) determinants exposed on the surface of the intact HTLV-III-infected cell are employed. Viable cells are reacted first with the anti-envelope protein antibody followed by a second fluorescent-labeled antibody that will react with the first unlabeled antibody. Details of the technique are described in Cell 39:327–337, 1984 (hereby incorporated by reference). Expression and quantitation of the amount of viral glycoprotein (fluorescein-labeled) on the cell surface is determined by Fluorescence Activated Cell Sorting (FACS).

An alteration in the size of the viral glycoproteins detected by Western blotting and/or immune precipitation, indicates that castanospermine. interrupts the normal carbohydrate processing of the HTLV-III viral glycoproteins, presumably in the rough endoplasmic reticulum at an early stage of carbohydrate remodeling. As mentioned above, such atypical viral structures represent relatively large uncleaved precursor proteins or abnormally glycosylated env proteins. A decreased cell surface fluorescence by FACS analysis indicates that the viral glycoproteins are not completely processed and are not expressed on the cell surface.

EXAMPLE 2

Effect of castanospermine on the production of HTLV-III virions.

HTLV-III infected H9 cells (or CEM cells) are grown in the presence or absence of castanospermine as described above. To determine whether the production of virus particles is decreased by castanospermine, cell-free supernatants are prepared and assayed for the presence of reverse transcriptase activity as described in Science 224:497–500, 1984 (hereby incorporated by reference). To determine whether any virions produced in the presence of castanospermine contain the fully processed viral glycoproteins, concentrated virus are banded in a sucrose gradient (also as described in the above publication), and the presence of viral proteins is assayed by polyacrylamide gel electrophoresis followed by staining the gel with a sensitive silver stain. Western blotting may also be used to detect the viral glycoproteins. These protocols can be used to select the dosage of castanospermine sufficient to prevent virus production and, alternatively, to determine whether virus particles produced in the presence of castanospermine lack the envelope proteins. Particles lacking envelope proteins are probably noninfectious. The infectivity of any virus particles produced in the presence of castanospermine can be assayed as described in Science 226:172–174, 1984 (hereby incorporated by reference).

EXAMPLE 3

Influence of castanospermine on the cytopathic effect of HTLV-III.

The inhibition of cytopathic effect exerted by HTLV-III-bearing H9 cells against a normal helper-inducer T-cell clone (YTA1) by castanospermine is determined by adaptation of a protocol described in Science 226:172–174, 1984.

YTA1 cells ($2 \times 10^5$) grown under the described conditions are exposed to castanospermine at various concentrations (10 to 500 µg/ml) for 24 hours in culture tubes (Falcon 3033) containing 2 ml of 15 percent (by volume) TCGF (Cellular Products) in the culture medium [RPMI 1640 supplemented with 15 percent heat-inactivated fetal calf serum, 4 mM L-glutamine, penicillin (50 unit/ml), and streptomycin (50 µg/ml)]. Culture tubes are kept at 37° C. in humidified air containing five percent $CO_2$. Then these YTA1 cells are added with an equal number of irradiated (10,000 rad) HTLV-III-bearing H9 or uninfected H9 cells. Control cells are cultured without any cells added. Cells are: continuously exposed to castanospermine and TCGF. The assays are performed in duplicate.

Measurement is made of the number of viable YTA1 cells per castanospermine concentration. On days 6, 8, and 10, the viable cells are counted in a hemacytometer under the microscope by the trypan blue exclusion method. When cultured alone in the presence of TCGF, none of the irradiated HTLV-III-bearing H9 or irradiated uninfected H9 cells are alive on day six in culture and would not be counted in the assay. Furthermore, normal YTA1 cells can be readily distinguished from neoplastic H9 cells by morphology.

EXAMPLE 4

Effect of castanospermine on HTLV-III infectivity in H9 cells.

To determine whether castanospermine blocks the expression of the OKT4 antigen that serves as a receptor for human T-lymphotrophic vital infection, cloned H9 cells are incubated in castanospermine prior to exposure to HTLV-III virus.

A modification of the protocol described in Science 226:172–174, 1984, is employed: The target H9 cells are exposed to castanospermine (10, 20, 40, 80 µg/ml) for 24 hours, then to polybrene (2 µg/ml) for 30 minutes before HTLV-III infection; control H9 cells are treated similarly but are not exposed to the drug. The H9 calls are then centrifuged (800g) and exposed to HTLV-III virus (0.5 ml containing $7.5 \times 10^7$ viral particles) for 60 minutes (again in the absence or presence of the above concentrations of castanospermine) and finally centrifuged (800g) and resuspended in fresh culture medium lacking castanospermine [RPMI 1640 supplemented with 20 percent heat-inactivated fetal calf serum, 4 mM L-glutamine, penicillin (50 unit/ml), and streptomycin (50 µg/ml)] and cultured in flasks at 37° C. in humidified air containing five percent $CO_2$. The cells are continuously exposed to castanospermine for 24 hours before and during the infection process. On days 4, 5, and 6 in culture, the percentage of the target H9 cells containing $p24^{gag}$ protein of HTLV-III$_B$ is determined by indirect immunofluorescence microscopy as described in Science 226:172–174, 1984. Cells are washed with phosphate-buffered saline (PBS) and suspended in the same buffer at a concentration of $10^6$ cells per milliliter. Approximately 50 µl of cell suspension is placed on a slide, air-dried, and fixed in acetone for ten minutes at room temperature. Slides are stored at –20° C. until used. Twenty microliters of rabbit antiserum to the $p24^{gag}$ protein of HTLV-III (diluted 1:2000 in PBS) are applied to these preparations and incubated for 50 minutes at 37° C. Then fluorescein-conjugated goat antiserum to rabbit immunoglobulin G (Capped is diluted and applied to the fixed cells for 30 minutes at room temperature. Slides are then washed extensively before microscopic examination under ultraviolet illumination.

Comparison is made of the HTLV-III infectivity rates, as indicated by the number of fluorescent cells, in the castanospermine-treated cells relative to the untreated controls. A reduction or prevention of HTLV-III infection indicates that castanospermine blocks the expression of the OKT4 antigen on the target cells. Direct analysis of the cell surface expression of the OKT4 antigen in the presence or absence of castanospermine can be made by viable cell fluorescence assays using a monoclonal antibody to the OKT4 antigen While the present invention has been described in conjunction with a preferred embodiment and specific examples, one of ordinary skill after reading the foregoing specification will be able to effect various changes, substitutions of equivalents, and other alterations to the methods and composition set forth herein. It is therefore intended that the protection granted by Letters Patent hereon be limited only to the definition contained in the appended claims and equivalents thereof.

The embodiments of the invention in which an exclusive property or privilege is claimed are defined as follows:

1. A method of regulating the replication of a nondefective retrovirus in a mammalian host in vivo comprising the step of administering to said host a therapeutically effective amount of a glucosidase I inhibitor.

2. The method of claim 1, wherein the glucosidase I inhibitor is selected from the group consisting of castanospermine, N-methyl-1-deoxynojirimycin, 1-deoxynojirimycin, and 2,5-dihydroxymethyl-3,4-dihydroxypyrrolidine.

3. The method of claim 2, wherein the glucosidase I inhibitor is castanospermine.

4. The method of claim 1, wherein the retrovirus is a human T-lymphotrophic virus.

5. The method of claim 4, wherein the retrovirus is selected from among HTLV-I, HTLV-II, and HTLV-III.

6. The method of claim 4, wherein the retrovirus is selected from the AIDS-associated retrovirus family.

7. The method of claim 1, wherein the retrovirus is the aetiological agent of feline leukemia, equine infectious anemia, or chronic lentiviral diseases.

8. The method of claim 1, comprising the step of administering the glucosidase I inhibitor in combination with a hematopoietic growth factor.

9. The method of claim 8, wherein the hematopoietic growth factor is selected from one or more of the group consisting of GM-CSF, G-CSF, M-CSF, and multi-CSF.

10. The method of claim 9, wherein the hematopoietic growth factor comprises GM-CSF.

11. The method of claim 1, comprising the step of administering the glucosidase I inhibitor in combination with an antibody to retroviral protein or glycoprotein.

12. The method of claim 1, comprising the step of administering the glucosidase I inhibitor in combination with retroviral protein or glycoprotein.

* * * * *

UNITED STATES PATENT AND TRADEMARK OFFICE
CERTIFICATE OF CORRECTION

PATENT NO. : 5,643,888
DATED : July 1, 1997
INVENTOR(S) : L.R. Rohrschneider

It is certified that error appears in the above-indentified patent and that said Letters Patent is hereby corrected as shown below:

ON THE TITLE PAGE ;

ITEM:

| | | |
|---|---|---|
| [56] Pg. 1, col. 1 | Refs. Cited Other Publs. Item 3 | "Inhibitors" should read --inhibitors-- |
| [56] Pg. 1, col. 2 | Refs. Cited Other Publs. Item 7 | "inihibitors" should read --inhibitors-- |
| [56] Pg. 1, col. 2 | Refs. Cited Other Publs. Item 18 | "2, 5-Dihydroxymethyl-3, 4-dihydroxypyrrolidine" should read --2,5-Dihydroxymethyl-3,4-dihydroxypyrrolidine-- |
| [56] Pg. 2, col. 1 | Refs. Cited Other Publs. Item 19 | After "Sindbis" insert --virus, -- |
| [56] Pg. 2, col. 1 | Refs. Cited. Other Publs. Item 23 | Delete "Aug." (duplicate occurrence) |
| [56] Pg. 2, col. 1 | Refs. Cited Other Publs. Item 29 | "formulation" should read --formation-- |

UNITED STATES PATENT AND TRADEMARK OFFICE
CERTIFICATE OF CORRECTION

PATENT NO. : 5,643,888
DATED : July 1, 1997
INVENTOR(S) : L.R. Rohrschneider

It is certified that error appears in the above-indentified patent and that said Letters Patent is hereby corrected as shown below:

[56] Pg. 2, col. 1  Refs. Cited Other Publs. Item 34  "αglucosidase" should read --α-glucosidase--

[56] Pg. 2, col. 2  Refs. Cited Other Publs. Item 39  "FEBS letters" should read --FEBS Letters--

[56] Pg. 2, col. 2  Refs. Cited Other Publs. Item 42  "mice;" should read --mice:--

[56] Pg. 2, col. 2  Refs. Cited Other Publs. Item 51  "chemistry" should read --Chemistry--

[56] Pg. 2, col. 2  Refs. Cited Other Publs. Item 54  "βhexosaminidase snthesized" should read --β-hexosaminidase synthesized--

UNITED STATES PATENT AND TRADEMARK OFFICE
CERTIFICATE OF CORRECTION

PATENT NO. : 5,643,888  Page 3 of 7
DATED : July 1, 1997
INVENTOR(S) : L.R. Rohrschneider It is certified that error appears in the above-indentified patent and that said Letters Patent is hereby corrected as shown below:

| | | |
|---|---|---|
| [56]<br>Pg. 3, col. 1 | Refs. Cited<br>Other Publs.<br>Item 57 | "αglucosidase" should read --α-glucosidase-- |
| [56]<br>Pg. 3, col. 1 | Refs. Cited<br>Other Publs.<br>Item 67 | "immunodefciency" should read --immunodeficiency-- |
| [56]<br>Pg. 3, col. 1 | Refs. Cited<br>Other Publs.<br>Item 68 | "immunodefiency" should read --immunodeficiency-- |
| [56]<br>Pg. 3, col. 1 | Refs. Cited<br>Other Publs.<br>Item 69 | "research" should read --Research-- |
| [56]<br>Pg. 3, col. 2 | Refs. Cited<br>Other Publs.<br>Item 80 | ".I.M." should read --I.M.-- |
| [56]<br>Pg. 3, col. 2 | Refs. Cited<br>Other Publs.<br>Item 81 | After "30(suppl 1)" insert --:-- |
| 1 | 30 | "sad" should read --and-- |

UNITED STATES PATENT AND TRADEMARK OFFICE
CERTIFICATE OF CORRECTION

PATENT NO. : 5,643,888
DATED : July 1, 1997
INVENTOR(S) : L.R. Rohrschneider

It is certified that error appears in the above-indentified patent and that said Letters Patent is hereby corrected as shown below:

| COLUMN | LINE | ERROR |
|---|---|---|
| 1 | 33 | "poI," should read --pol,-- |
| 1 | 56 | "Impaired" should read --impaired-- |
| 1 | 61 | After "helper" insert --lymphocytes;-- |
| 1 | 61 | "HTLV-III" should read --HTLV-III-- |
| 1 | 64 | "pro-AIDS" should read --pre-AIDS-- |
| 2 | 5 | "immunosuppressire" should read --immunosuppressive-- |
| 2 | 11 | "cycopathic" should read --cytopathic-- |
| 2 | 24 | "eases" should read --cases-- |
| 2 | 50 | "tousle," should read --muscle,-- |
| 2 | 56 | "vital" should read --viral-- |
| 2 | 60 | "any" should read --env-- |
| 3 | 13 | "any" should read --env-- |
| 3 | 20 | "Sciences" should read --Science-- |

UNITED STATES PATENT AND TRADEMARK OFFICE
CERTIFICATE OF CORRECTION

PATENT NO. : 5,643,888  
DATED : July 1, 1997  
INVENTOR(S) : L.R. Rohrschneider It is certified that error appears in the above-indentified patent and that said Letters Patent is hereby corrected as shown below:

| COLUMN | LINE | ERROR |
|---|---|---|
| 3 | 24 | "vital" should read --viral-- |
| 3 | 50 | "vital" should read --viral-- |
| 4 | 2 | ""B-cells"," should read --B cells,-- |
| 4 | 3 | "erythroeytes" should read --erythrocytes-- |
| 4 | 45 | After "populations" insert --,-- |
| 4 | 53 | "lineage" should read --lineages-- |
| 4 | 54 | "castanospermines," should read --castanospermine-- |
| 4 | 59-60 | "hematopoietie cell is" should read --hematopoietic cells-- |
| 5 | 10 | "monoclonal" should read --monoclonals-- |
| 5 | 12 | "vital" should read --viral-- |
| 5 | 36 | "gp 120" should read --gp120-- |
| 5 | 38 | "immune precipitation" should read --immunoprecipitation-- |

UNITED STATES PATENT AND TRADEMARK OFFICE
CERTIFICATE OF CORRECTION

PATENT NO. : 5,643,888  
DATED : July 1, 1997  
INVENTOR(S) : L.R. Rohrschneider It is certified that error appears in the above-indentified patent and that said Letters Patent is hereby corrected as shown below:

| COLUMN | LINE | ERROR |
|---|---|---|
| 5 | 45 | "$^{125}$-I labeled;" should read --$^{125}$I-labeled-- |
| 5 | 47-48 | "immune precipitation;" should read --immunoprecipitation-- |
| 5 | 51 | "immune precipitation" should read --immunoprecipitation-- |
| 5 | 65 | "vital" should read --viral-- |
| 6 | 1 | "vital" should read --viral-- |
| 6 | 2 | "immune precipitation," should read --immunoprecipitation-- |
| 6 | 3 | After "castanospermine" delete "." |
| 6 | 4 | "vital" should read --viral-- |
| 6 | 7 | "vital" should read --viral-- |
| 6 | 59 | After "Cells are" delete ":" |
| 6 | 60 | After "assays are" insert --all-- |
| 7 | 11 | "vital" should read --viral-- |

UNITED STATES PATENT AND TRADEMARK OFFICE
CERTIFICATE OF CORRECTION

PATENT NO. : 5,643,888
DATED : July 1, 1997
INVENTOR(S) : L.R. Rohrschneider

It is certified that error appears in the above-indentified patent and that said Letters Patent is hereby corrected as shown below:

| COLUMN | LINE | ERROR |
|---|---|---|
| 7 | 19 | "calls" should read --cells-- |
| 7 | 43 | "(Capped" should read --(Cappel)-- |
| 8 | 4 | After "antigen" insert --.-- |
| 8 | 10 | "composition" should read --compositions-- |

Signed and Sealed this

Twenty-third Day of December, 1997

Attest:

Attesting Officer

BRUCE LEHMAN

Commissioner of Patents and Trademarks